United States Patent
Heyer et al.

(12)

(10) Patent No.: US 6,255,562 B1
(45) Date of Patent: Jul. 3, 2001

(54) PROCESS FOR PRODUCING TRANSGENIC INULIN-GENERATING PLANTS

(75) Inventors: Arnd G. Heyer; Regina Wendenburg, both of Berlin (DE)

(73) Assignees: Sudzucker Aktiengesellschaft; KWS Saat AG, both of (DE)

( * ) Notice: Subject to any disclaimer, the term of this patent is extended or adjusted under 35 U.S.C. 154(b) by 0 days.

(21) Appl. No.: 09/180,143

(22) PCT Filed: Apr. 29, 1997

(86) PCT No.: PCT/EP97/02195

§ 371 Date: Nov. 3, 1998

§ 102(e) Date: Nov. 3, 1998

(87) PCT Pub. No.: WO97/42331

PCT Pub. Date: Nov. 13, 1997

(30) Foreign Application Priority Data

May 3, 1996 (DE) ............................... 196 17 687

(51) Int. Cl.[7] ............ C12N 15/31; C12N 15/54; C12N 15/82; C12P 19/04; A01H 5/00
(52) U.S. Cl. ............ 800/284; 800/278; 800/287; 800/288; 800/317.2; 800/320; 800/320.1; 800/320.2; 800/320.3; 435/69.7; 435/69.8; 435/101; 435/193; 435/252.3; 435/320.1; 435/412; 435/417; 435/419; 435/468
(58) Field of Search .................. 536/23.2, 23.4, 536/23.7; 435/69.7, 69.8, 101, 193, 252.3, 320.1, 419, 412, 417, 468; 800/278, 284, 287, 288, 317.2, 320, 320.1, 320.2, 320.3

(56) References Cited

FOREIGN PATENT DOCUMENTS

| 2142308 | 3/1994 | (CA) . |
|---|---|---|
| 4227061 | 2/1994 | (DE) . |
| 9414970 | 7/1994 | (WO) . |
| 9513389 | 5/1995 | (WO) . |
| 9601904 | 1/1996 | (WO) . |

OTHER PUBLICATIONS

Turk et al. New Phytol. 136: 29–38, 1997.*
S. Rosahl et al., "Isolation and Characterization of a Gene from *Solanum tuberosum* Encoding Patatin, the Major Storage Protein of Potato Tubers", Mol. Gen. Genet 203:214–220 (1986).
U. Sonnewald et al., "Expression of Mutant Patatin Protein in Transgenic Tobacco Plants: Role of Glycans and Intracellular Location", The Plant Journal 2:345–355 (1990).
U. Sonnewald et al., "Transgenic Tobacco Plants Expressing Yeast–derived Invertase in Either the Cytosol, Vacuole or Apoplast: a Powerful Tool for Studying Sucrose Metabolism and Sink/Source Interactions", *The Plant Journal* 1(1):95–106 (1991).
K. Nakamura et al., "Protein Targeting to the Vacuole in Plant Cells", Plant Physiol. 101:1–5 (1993).
Rocha–Sosa et al. EMBO J. 8(1):23–29 (1989).

* cited by examiner

Primary Examiner—David T. Fox
(74) Attorney, Agent, or Firm—Ostrolenk, Faber, Gerb & Soffen, LLP

(57) ABSTRACT

The present invention relates to a process for preparing recombinantly modified, inulin-producing plants, to the DNA sequences which are used in this context and to the transformed plants which are obtained.

27 Claims, 6 Drawing Sheets

Northern blot analysis of the contents of ftf mRNA in selected transformants of the cell lines B33cftf, B33aftf, B33v1ftf and B33v2ftf. C: Control RNA of the untransformed starting cell line

PROCESS FOR PRODUCING TRANSGENIC INULIN-GENERATING PLANTS

This application is a 371 of PCT/EP97/02195 filed Apr. 29, 1997.

FIELD OF THE INVENTION

The present invention relates to a process for preparing recombinantly modified plants which produce high molecular weight inulin, to means for implementing this process and the plants which can be obtained using these means and process, and to the high molecular weight inulin which is contained in the plants.

BACKGROUND OF THE INVENTION

High molecular weight, water-soluble, linear polymers, for example polyacrylates and polymethyl acrylates, are known. These polymers are employed, for example, for increasing the viscosity of aqueous systems, as a suspending agent, for accelerating sedimentation and complexing, and in super-absorbers for binding water and in lacquers and varnishes which can be diluted in water. The fact that these products are not biologically degradable proves to be a disadvantage. Derivatized, highly polymerized polysaccharides come into consideration as an alternative. These polysaccharides have to date been obtained biotechnologically, by means of fermentation and transglycosylation. However, for economic reasons, fermentatively produced polymers are not suitable for relatively large-scale applications. For this reason, attempts have been made for some time now to produce linear, water-soluble polymers, such as inulin, in plants.

Inulin, which is a β-2-1-linked polyfructan, can be detected as a storage carbohydrate in some dicotyledonous higher plants and is present at a molecular weight of 5–50 kD. In addition, among the bacteria, some Gram-positive and Gram-negative bacterial species are known to synthesize a related fructan polymer, i.e. the β-2-6-linked levan, using so-called levan sucrases. Polyfructans which are formed in bacteria exhibit substantially higher molecular weights of up to 2000 kD. At present, only one Gram-positive bacterium, i.e. Streptococcus mutans, has been described which uses an ftf (fructosyltransferase) gene to form inulin on the basis of sucrose (Shiroza and Kuramitsu, J. Bacteriology (1988) 170, 810 to 816).

Processes which use biotechnological methods to alter the carbohydrate concentration and/or the composition of the carbohydrates in transgenic plants are known. PCT/US89/02729 describes one option for producing carbohydrate polymers, in particular dextran or polyfructose, in transgenic plants, in particular their fruit. The use of levan sucrase or dextran sucrase from a variety of microorganisms is proposed for producing these plants. The patent does not demonstrate the formation of the active enzymes nor that of levan or dextran, and nor does it demonstrate the preparation of transgenic plants.

PCT/EP93/02110 discloses a process for preparing polyfructose-producing transgenic plants which contain the lsc gene for a levan sucrase from a Gram-negative bacterium.

PCT/NL93/00279 discloses the transformation of plants with chimeric genes which contain the sacB gene from Bacillus subtilis or the ftf gene from Streptococcus mutans. In the case of the sacB gene, a modification of the 5'-untranslated region of the bacterial gene is additionally recommended for increasing the level of expression in transformed plants. No sequence modifications for improving expression are described in the case of the fructosyltransferase gene from Streptococcus mutans. As a result, the level at which the fructosyltransferase is expressed is comparatively low.

SUMMARY OF THE INVENTION

Figure 1:
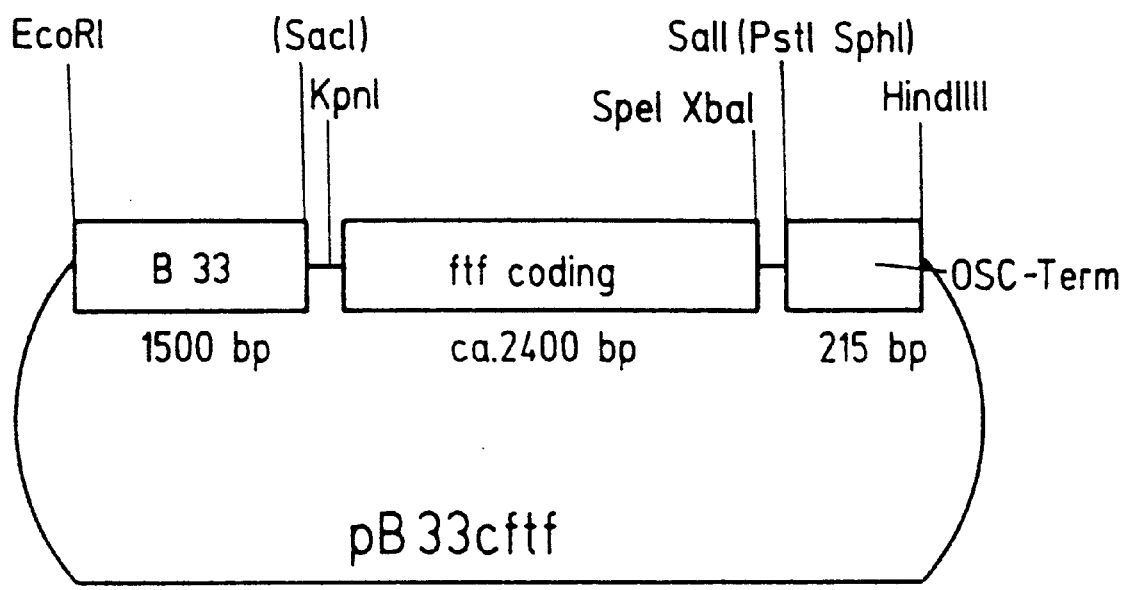
FIG. 1 depicts the construction of plasmid pB33cftf.

The present invention is consequently based on the technical problem of providing a process and means for preparing high molecular weight inulin in plants, which process and agents enable inulin to be produced in large quantity in plants in a simple and economically favorable manner.

The solution to this technical problem lies in the provision of a modified fructosyltransferase gene, in particular a gene in which a region, preferably the aminoterminal region, of a known fructosyltransferase gene is replaced with a region of a patatin gene and/or of another gene. The preferred modification, which is envisaged in accordance with the invention, of the sequence of the known fructosyltransferase gene consequently consists in replacing the coding region of the aminoterminal region of a fructosyltransferase gene with the aminoterminal region of a patatin gene and/or of another gene. The other gene can, for example, be the carboxypeptidase Y gene (cpy gene) or the lacZ gene. An embodiment in which the aminoterminal region of the fructosyltransferase gene is only replaced with a region of the patatin gene is preferred. Surprisingly, a fructosyltransferase gene which has been modified in such a way can be expressed efficiently in higher plants, with high molecular weight inulin being obtained in large quantity. Particularly advantageously, no extensive modification of the sequence, or neosynthesis, of the original fructosyltransferase gene is required.

In connection with the present invention, a fructosyltransferase gene is understood as being the coding DNA sequence of a gene whose gene product exhibits a sucrose: β-D-fructosyltransferase activity. A gene of this nature can be of plant, animal, microbial or synthetic origin. According to the invention, modified fructosyltransferase genes are understood as being the coding DNA sequences of modified genes whose gene products exhibit a sucrose: β-D-fructosyltransferase activity and are able to form β-2-1-linked polyfructans, that is, in particular, inulins. The gene products of the modified genes consequently exhibit the above-defined biological activity of an inulin sucrase. The term modification is understood as meaning all the manipulations which are carried out on a DNA sequence, for example nucleotide substitutions, nucleotide deletions, nucleotide inversions or nucleotide additions. The aminoterminal region of a gene is understood as being that region of the coding DNA sequence which encodes the aminoterminal region of the gene product, with it being possible for the aminoterminal region of the gene to encompass many codons or only a few codons, or else only the start codon alone. A patatin gene is understood as being a gene which belongs to the patatin gene family and which can, for example, be a class I or class II patatin gene (Rocha-Sosa et al., EMBO J (1989) 8, 23–29). A patatin gene is also understood as meaning patatin-analogous genes which exhibit sequence homology with, and/or functional similarity to, the patatin genes. While the patatin gene which is used in accordance with the invention is preferably derived from potato, it can also be of synthetic or other origin.

Finally, high molecular weight inulin is understood, according to the invention, as being an inulin which has a molecular weight of more than 1.5 million daltons.

DETAILED DESCRIPTION OF THE INVENTION

The solution to the above-mentioned technical problem is provided, in particular, by the gene which is characterized in the main claim, vectors which exhibit this gene, transformation methods which use these vectors, the plants and inulins which are obtained using this process, and methods for isolating the inulin, which is formed in accordance with the invention, from the novel plants. The subclaims relate to advantageous embodiments of the invention.

In a first embodiment, the invention relates to a modified fructosyltransferase gene in which the aminoterminal region of a fructosyltransferase gene is replaced, at least partially, with the region of another gene, namely a patatin gene. Apart from the replacement of the original amino-terminal region of the fructosyltransferase gene with a region of the patatin gene, preferably the aminoterminal region, the fructosyltransferase gene can, of course, also exhibit further modifications and/or be prepared in a fully synthetic manner.

However, the invention also relates to all other modifications of a fructosyltransferase gene, provided the gene product which is formed can produce high molecular weight inulin in plants.

In a particularly preferred embodiment of the invention, it is provided that the aminoterminal region of the fructosyltransferase gene is replaced with sequences from plant or bacterial genes or genes from yeast, in particular the patatin gene from, preferably, potato and optionally another gene, for example the cpy gene from yeast or the lacZ gene from Escherichia coli.

It is particularly preferably provided that the plant gene is the patatin B33 gene from potato. In particular, the invention envisages replacing the aminoterminal region of the fructosyltransferase gene with signal peptide-encoding signal sequences of the patatin gene. Signal sequences of the patatin gene, in particular of the potato patatin B33 gene, which can be employed in accordance with the invention encode signal peptides for uptake into the endoplasmic reticulum or signal peptides which permit location of the gene product in the vacuole. The invention consequently relates to modified fructosyltransferase genes in which the modification of the fructosyltransferase gene can consist in the aminoterminal region of the fructosyltransferase gene being replaced with signal sequences of plant genes, such as, for example, the patatin gene from potato. The invention also encompasses modified fructosyltransferase genes in which the aminoterminal region of the fructosyltransferase gene is replaced with regions, in particular aminoterminal regions, of different genes, for example the aminoterminal region of the patatin gene and of the lacZ gene. Particular preference is given to the said aminoterminal region of the lacZ gene encoding aminoterminal amino acids 21 to 30 of β-galactosidase. The invention naturally also encompasses modified fructosyltransferase genes in which the aminoterminal region of the modified fructosyltransferase gene is provided by regions of different plant genes and genes from yeast, for example the cpy gene (carboxypeptidase Y) and the potato patatin gene. In the latter two cases, preference is given to the signal sequence which encodes the signal peptide from the patatin gene being arranged upstream (5') of the sequence of the cpy gene or of the lacZ gene.

A further embodiment of the invention provides that the fructosyltransferase is derived from Streptococcus mutans. However, the invention naturally also relates to the use of other fructosyltransferases, as long as they are able, in the modified form which is stipulated in accordance with the invention, to produce inulins.

In a particularly preferred embodiment of the invention, the aminoterminal region of the fructosyltransferase gene to be replaced is a region which encodes its signal peptide. In connection with the present invention, a signal peptide-encoding region is understood as being the region between the translation start and the beginning of the DNA sequence which encodes the mature, processed protein.

In one embodiment, the invention relates to a modified fructosyltransferase gene which exhibits a signal sequence which encodes a signal peptide for uptake of the modified gene into the endoplasmic reticulum of a eukaryotic cell. The invention consequently envisages that a modified gene of the invention can be provided with signal sequences which permit location of the gene product in particular compartments of the cell. The signal sequence of a patatin gene, in particular of patatin gene B33, preferably from potato, is particularly preferred in accordance with the invention. As has been explained, the signal sequence can be fused onto the modified fructosyltransferase gene in addition to a modification of the fructosyltransferase gene which has already taken place, or the signal sequence is fused directly to the fructosyltransferase gene whose aminoterminal region has been truncated. Consequently, in both the preferred embodiments, it is envisaged, according to the invention, that the aminoterminal region of the fructosyltransferase gene is replaced with at least a part of the patatin gene and that, where appropriate, sequences from other genes, for example the lacZ gene or the cpy gene, are also additionally present in the aminoterminal region of the modified fructosyltransferase gene. Using the signal sequence, from the aminoterminal region of the patatin B33 gene, which encodes the signal peptide for uptake into the endoplasmic reticulum achieves translocation of the gene product into the apoplastic space. As a result, the synthesis of the high molecular weight inulin is carried out at this site, which means that specific changes in the carbohydrate composition of the transgenic plant can be effected. Naturally, other signal sequences can also be used in accordance with the invention. Thus, signal sequences which encode signal peptides which lead to the uptake of a protein into the endoplasmic reticulum, and which can be detected by the fact that they can be identified in the precursor proteins but not in processed, mature proteins, are particularly suitable. Thus, as is known, signal peptides are proteolytically removed during the uptake into the endoplasmic reticulum. In a further preferred embodiment, the invention provides that the modified fructosyltransferase gene is fused to, or exhibits, a signal sequence which encodes a signal peptide for uptake into the endoplasmic reticulum of a eukaryotic cell and subsequent guidance into the vacuole. The use of a signal peptide for locating the gene product in a vacuole is advantageous insofar as this can also bring about specific changes in the carbohydrate composition of the resulting transgenic plants. For example, use can be made, according to the invention, of signal peptides for locating barley lectin in the vacuole (Raikhel and Lerner, Dev Genet (1991) 12, 255–260), signal sequences which encode 43 amino acids in the aminoterminal region of the mature bean phytohemagglutinin (Tague et al., Plant cell (1990) 2, 533–546) and signal sequences from a potato patatin gene.

According to the invention, preference is given to a modification of the fructosyltransferase gene in which a signal sequence of the patatin B33 gene, in particular a signal sequence which encodes the 60 aminoterminal amino acids of the propeptide (Rosahl et al., Mol Gen Genet (1986) 203, 214–220), that is nt 736 to 855, is used. This signal sequence at least partially replaces the aminoterminal region of the fructosyltransferase gene, where appropriate together with regions of other genes. In the context of the present invention, this sequence is termed an extended B33 signal sequence. This sequence can be obtained both as a fragment of potato genomic DNA and from cDNA for the transcript of the B33 gene. Fusion of the extended B33 signal sequence to the modified gene of the invention or to the fructosyltransferase gene to be modified leads to the uptake of its gene product into the vacuole and thereby to a specific change in the carbohydrate composition of the resulting transgenic plant.

The invention also relates to the use of this extended B33 signal sequence or, respectively, of the peptide which it encodes for transporting any other gene products into plant vacuoles.

The invention also relates to a vector, in particular a plasmid, which contains a modified fructosyltransferase gene. In particular, the invention relates to a vector or a plasmid which contains a modified fructosyltransferase gene which is under the control of a promoter which is active in plants, in particular an organ-specific promoter. As is known, sucrose is the substrate for fructosyltransferase, which means that it is advantageous to produce high molecular weight inulin particularly in those plant tissues or plant organs which store large quantities of sucrose. These include, for example, the beet of sugar beet or the stem of sugar cane. According to the invention, expression of the modified fructosyltransferase gene in these organs can be achieved by using tissue-specific promoters. For example, the B33 promoter of the potato B33 gene can be used to achieve organ-specific expression in potato tubers or beets of sugar beets.

The invention also relates to a vector or a plasmid in which the 3' terminus of the modified fructosyltransferase gene is fused to a transcription termination sequence, for example the polyadenylation site of the Agrobacterium tumefaciens nos gene.

In a particularly preferred embodiment, the invention relates to the plasmids pB33cftf, that is a plasmid which contains the B33 promoter of the patatin gene, a lacZ-ftf gene fusion and a polyadenylation signal, pB33aftf, that is a plasmid which contains the B33 promoter of the patatin gene, a B33 signal sequence-lacZ-ftf gene fusion and a polyadenylation signal, pB33v1ftf, that is a plasmid which contains the B33 promoter of the patatin gene, an extended B33 signal sequence-lacZ-ftf gene fusion and a polyadenylation signal, and pB33v2ftf, that is a plasmid which contains the B33 promoter of the patatin gene, an extended B33 signal sequence-lacZ-ftf gene fusion (without intron in the signal sequence) and a polyadenylation signal (FIGS. 1 to 4). The invention naturally also relates to the gene fusions which are contained in the above-mentioned plasmids without using the lacz gene sequences which are located between the patatin sequences and the ftf sequences.

The invention also relates to prokaryotic and eukaryotic cells which contain a vector, a plasmid or a DNA sequence of the invention. In particular, the invention relates to the cells, for example bacterial cells or, preferably, plant cells which exhibit the novel vectors, plasmids or DNA sequences. These cells can contain the modified fructosyltransferase gene of the invention either transiently or, particularly preferably, stably integrated into their genome. In the context of the present invention, the novel plant cells are understood as being either those which were produced directly by the transformation event and, consequently, can be present in undifferentiated or differentiated form depending on the chosen transformation method, or plant cells which are differentiating or, respectively, which are fully differentiated.

The invention also relates to plants which contain at least one cell, preferably, however, a large number of cells, which exhibit(s) the novel fructosyltransferase gene or vectors or plasmids which contain this gene and as a result produce(s) high molecular weight inulin. The invention consequently makes it possible to provide plants of a very wide variety of species, genera, families, orders and classes which are able to produce high molecular weight inulin because of the modified fructosyltransferase gene which has been introduced into them. Since the known plants are not able to produce high molecular weight inulin, it is readily possible to demonstrate, for example by means of antibody tests, that the novel process has been successfully carried out. As compared with the little known inulin-producing plants, the advantages are gained that it is possible to specifically locate the inulin which is formed and that, in addition, an increase is achieved in the rate of expression and consequently in the quantity of inulin formed. Furthermore, the novel inulin which is produced by the gene, according to the invention, of bacterial origin exhibits a higher molecular weight than does plant inulin. In this case, too, successful transformation with the novel sequences can be demonstrated, for example, by means of compartment-specific antibody tests which can, where appropriate, be quantified.

The invention envisages, in particular, that the plant to be transformed is an economically useful plant, in particular a corn, rice, wheat, barley, sugar beet, sugar cane or potato plant.

The invention also relates to a process for preparing the above-mentioned plants, which process comprises the transformation of one or more plant cells with a vector or a plasmid of the invention, the integration of the modified fructosyltransferase gene, which is contained in this vector or plasmid, into the genome of the plant cell(s), and the regeneration of the plant cell(s) into intact, transformed, high molecular weight inulin-producing plants.

Finally, the invention relates to the high molecular weight inulin which is produced by the novel plants. As compared with inulin which occurs naturally in some plants, this inulin is also distinguished, in particular, by its high molecular weight of more than 1.5 million daltons.

The invention also relates to a process for obtaining inulin from the transformed plants, in particular from their vacuoles.

EXAMPLE 1

Preparation of Plasmid pB33cftf and Insertion of the Corresponding Construct Into the Potato Genome.

Plasmid pB33cftf contains the three fragments A, B and C in the binary vector pBin19-Hyg (Bevan, Nucl Acids Res (1984) 12, 8711, modified in accordance with Becker, Nucl Acids Res (1990) 18, 203) (see FIG. 1).

Fragment A encompasses the B33 promoter of potato patatin gene B33. It contains a DraI fragment (position: −1512 to position +14) of patatin gene B33 (Rocha-Sosa et al., EMBO J (1989) 8, 23–29) which is inserted between the EcoRI and SacI cleavage sites of the pBin19-Hyg polylinker.

Fragment B is a fusion of nt 780–3191 of the Streptococcus mutans ftf gene (Genbank EMBL Accession M18954) to a combination of nt 724–716 and nt 759–727 of the plasmid pBluescript KS, which represent aminoterminal amino acids 21–30 of β-galactosidase. An ATG start codon, which is used for translating the fusion product in plants, is produced in front of this sequence in association with the cloning. The sequence up to the fusion to nt 780 of the ftf gene is depicted below:

```
                                             (SEQ ID NO:1)
    AAGCTTGATGTACCGGGCCCCCCCTCGAGGTCGACGGTATCG
    |.......||.................................|
    724...716 759..........................727
``` nt 780–3191 of the ftf gene were isolated from plasmid pTS102 (Shiroza and Kuramitsu, J. Bacteriol. (1988) 170, 810–816) as an EarI-(filled-in with DNA polymerase)/BglII fragment. The fusion of this fragment of the ftf gene to the said DNA sequence replaces the original N terminus with the aminoterminal region of β-galactosidase.

Fragment C contains the polyadenylation signal of gene 3 (Agrobacterium tumefaciens octopine synthase gene) of the T-DNA of the Ti plasmid pTiAch 5 (Gielen et al., EMBO J. (1984) 3, 835–846), that is nucleotides 11749–11939, which was isolated from plasmid pAGV 40 (Herrera-Estrella et al., Nature (1983) 303, 209–213) as a Pvu II/HindIII fragment and, after the addition of SphI linkers, was cloned into the Pvu II cleavage site between the SphI and HindIII cleavage sites of the pBin19-Hyg polylinker.

Plasmid pB33cftf is approximately 14 kb in size.

The pB33cftf construct was introduced into potato plants. Intact plants were regenerated from transformed cells. Analysis of the tubers from a number of plants which were transformed with this gene clearly demonstrated the occurrence of inulin, which is to be attributed to expression of the novel gene.

EXAMPLE 2

Preparation of Plasmid pB33aftf and Insertion of the Corresponding Construct Into the Potato Genome.

Figure 2:
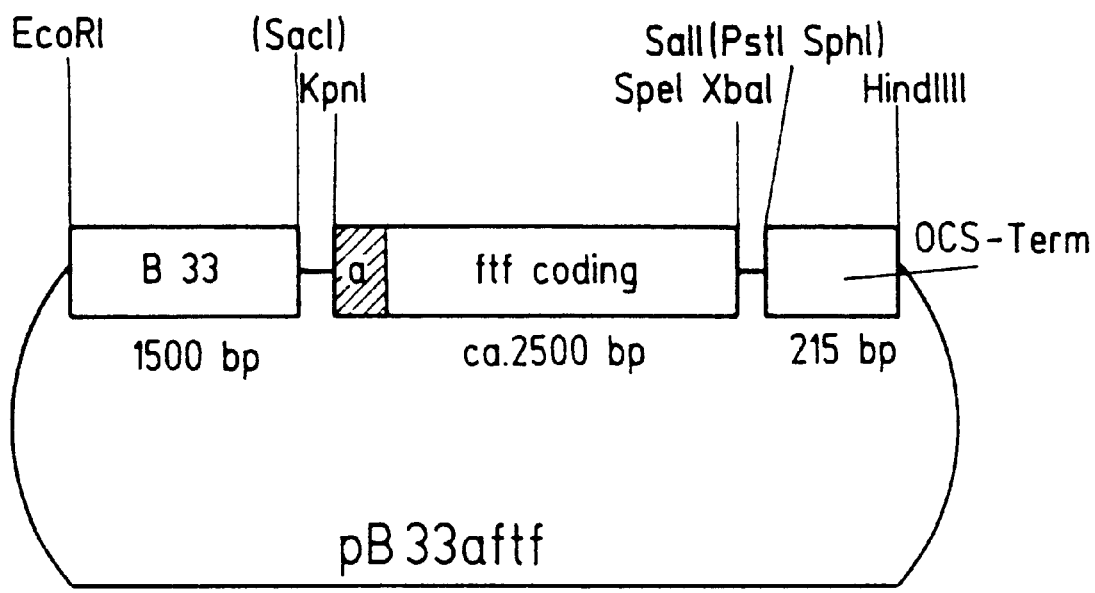
FIG. 2 depicts the construction of plasmid pB33aftf.

Plasmid pB33aftf contains the three fragments A, B and C in the binary vector pBin19-Hyg (Bevan, Nucl Acids Res (1984) 12, 8711, modified in accordance with Becker, Nucl Acids Res (1990) 18, 203) (see FIG. 2).

Fragment A encompasses the B33 promoter of potato patatin gene B33. It contains a DraI fragment (position: −1512 to position +14) of patatin gene B33 (Rocha-Sosa et al., EMBO J (1989) 8, 23–29) which is inserted between the EcoRI and SacI cleavage sites of the pBin19-Hyg polylinker.

Fragment B is a fusion of the modified Streptococcus mutans ftf gene (nt 780–3191, see Example 1) to nt 724 to 833 of patatin gene B33 by way of a sequence containing the nucleotides GTCGACGGTATCG (SEQ ID NO:2). This sequence (designated "a" in FIG. 2) contains the coding region for the signal peptide for uptake into the endoplasmic reticulum (ER) (Rosahl et al., Mol Gen Genet (1986) 203, 214–220; sequence derives from pcT58). Proteins which possess a signal sequence of this nature are firstly taken up into the ER and then exported into the apoplastic space.

Fragment C contains the polyadenylation signal of gene 3 (Agrobacterium tumefaciens octopine synthase gene) of the T-DNA of the Ti plasmid pTiAch 5 (Gielen et al., EMBO J. (1984) 3, 835–846), that is nucleotides 11749–11939, which was isolated from plasmid pAGV 40 (Herrera-Estrella et al., Nature (1983) 303, 209–213) as a Pvu II/HindIII fragment and, after the addition of SphI linkers, was cloned into the Pvu II cleavage site between the SphI and HindIII cleavage sites of the pBin19-Hyg polylinker.

Plasmid pB33aftf is approximately 14 kb in size.

The B33aftf construct was introduced into potato plants. Intact plants were regenerated from transformed cells. Analysis of the tubers from a number of plants which were transformed with this gene clearly demonstrated the occurrence of inulin, which is to be attributed to expression of the novel gene.

EXAMPLE 3

Preparation of Plasmid pB33v1ftf and Insertion of the Corresponding Constructs Into the Potato Genome.

Figure 3:
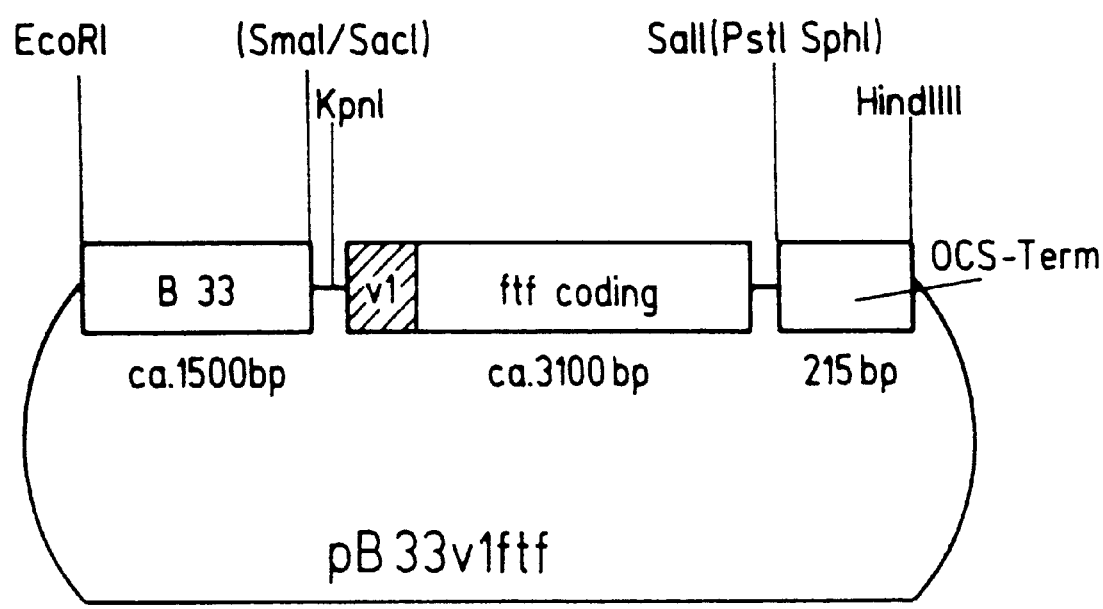
FIG. 3 depicts the construction of plasmid pB33v1ftf.

Plasmid pB33v1ftf contains the three fragments A, B and C in the binary vector pBin19-Hyg (Bevan, Nucl Acids Res (1984) 12, 8711, modified in accordance with Becker, Nucl Acids Res (1990) 18, 203) (see FIG. 3).

Fragment A encompasses the B33 promoter of potato patatin gene B33. It contains a DraI fragment (position: −1512 to position +14) of patatin gene B33 (Rocha-Sosa et al., EMBO J (1989) 8, 23–29) which is inserted between the EcoRI and SacI cleavage sites of the pBin19-Hyg polylinker.

Fragment B is a fusion of the modified Streptococcus mutans ftf gene (nt 780–3191, see Example 1) to nt 724 to 1399 of patatin gene B33 by way of a sequence containing the nucleotides GTCGACGGTATCG (SEQ ID NO:2). This sequence (designated "V1" in FIG. 3) contains the coding region for the signal peptide for uptake into the ER and also the subsequent information for a signal for further guidance into the vacuole (Rosahl et al., Mol Gen Genet (1986) 203, 214–220, sequence derives from pgT5). An intron is inserted into the coding region of this extended signal sequence. The nucleotide sequence of the intron is removed from the transcript of the chimeric gene by splicing. Proteins which possess a signal peptide of this nature are initially taken up into the ER and then transported into the vacuole.

Fragment C contains the polyadenylation signal of gene 3 (Agrobacterium tumefaciens octopine synthase gene) of the T-DNA of the Ti plasmid pTiAch 5 (Gielen et al., EMBO J. (1984) 3, 835–846), that is nucleotides 11749–11939, which was isolated from plasmid pAGV 40 (Herrera-Estrella et al., Nature (1983) 303, 209–213) as a Pvu II/HindIII fragment and, after the addition of SphI linkers, was cloned into the Pvu II cleavage site between the SphI and HindIII cleavage sites of the pBin19-Hyg polylinker.

Plasmid pB33v1ftf is approximately 14 kb in size.

Figure 6:
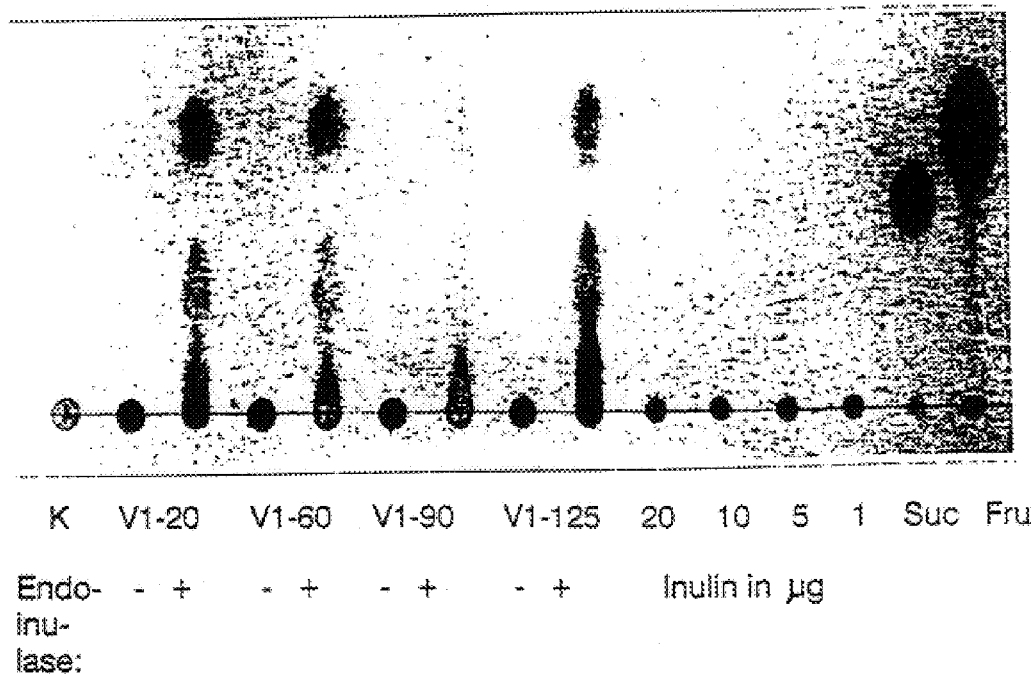
FIG. 6 depicts a thin layer chromatographic analysis of the inulin contents of tubers from a number of plants transformed with plasmid pB33v1ftf.

The B33v1ftf construct was introduced into potato plants. Intact plants were regenerated from transformed cells. Analysis of the tubers from a number of plants which were transformed with this gene clearly demonstrated the occurrence of inulin, which is to be attributed to expression of the novel gene (see FIG. 6).

EXAMPLE 4

Preparation of Plasmid pB33v2ftf and Insertion of the Corresponding Construct Into the Potato Genome.

Figure 4:
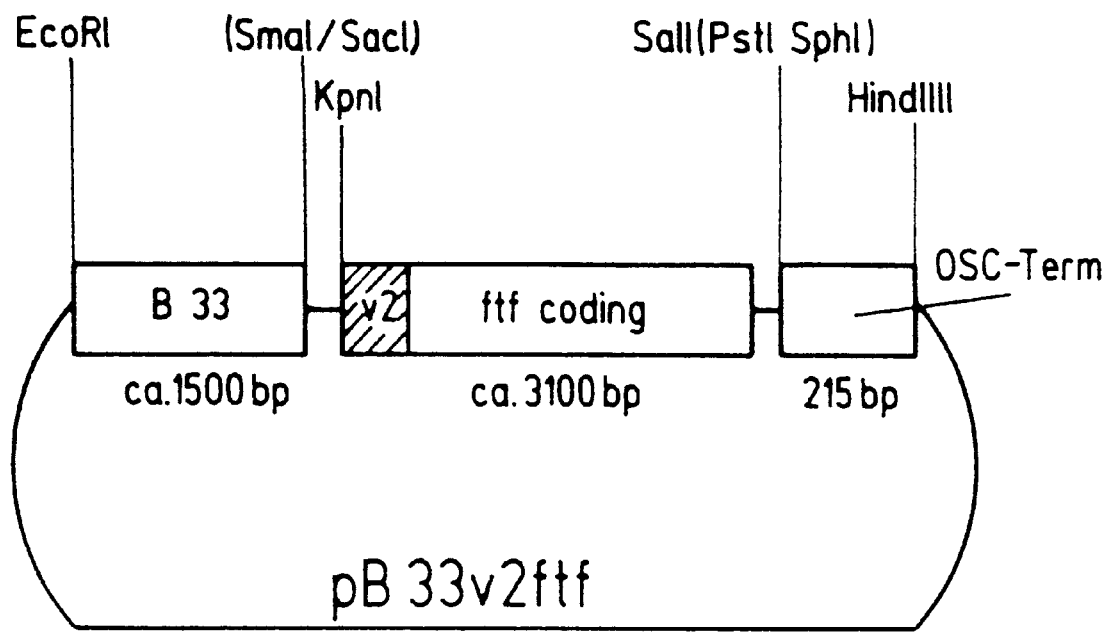
FIG. 4 depicts the construction of plasmid pB33v2ftf.
Figure 5:
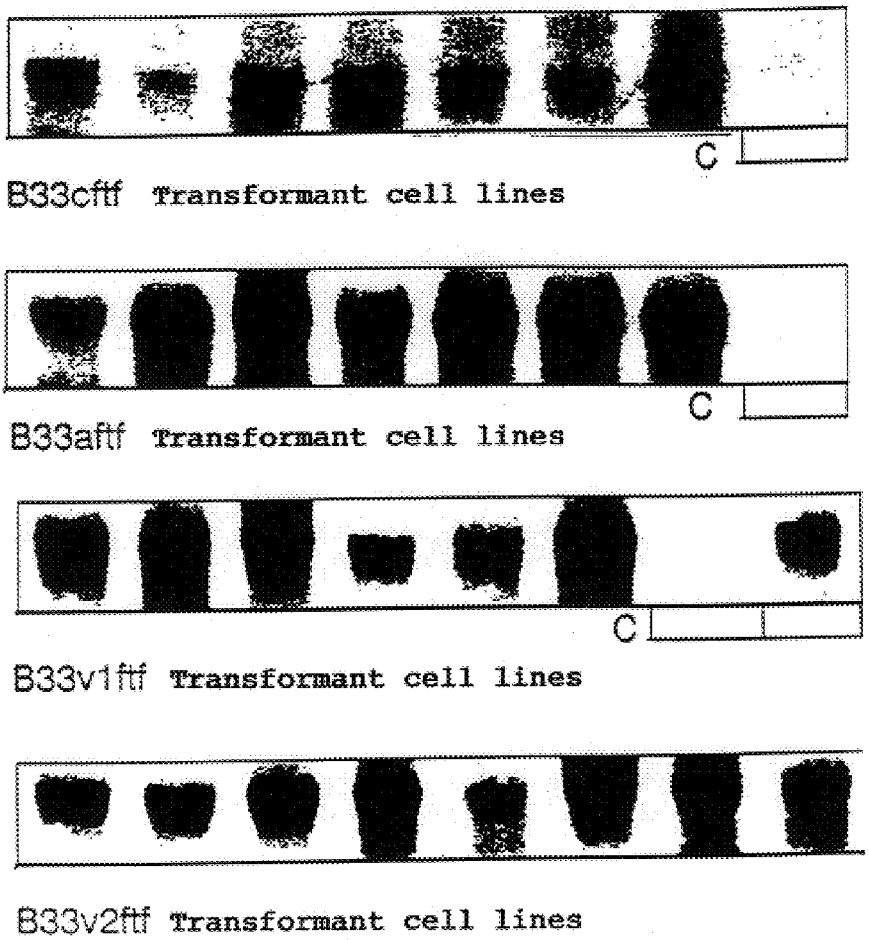
FIG. 5 depicts a Northern blot analysis of gene expression, i.e. of the contents of ftf mRNA in the tubers of selected transformants containing the novel constructs.

Plasmid pB33v2ftf contains the three fragments A, B and C in the binary vector pBin19-Hyg (Bevan, Nucl Acids Res (1984) 12, 8711, modified in accordance with Becker, Nucl Acids Res (1990) 18, 203) (see FIG. 4).

Fragment A encompasses the B33 promoter of potato patatin gene B33. It contains a DraI fragment (position:

−1512 to position +14) of patatin gene B33 (Rocha-Sosa et al., EMBO J (1989) 8, 23–29) which is inserted between the EcoRI and SacI cleavage sites of the pBin19-Hyg polylinker.

Fragment B is a fusion of the modified Streptococcus mutans ftf gene (nt 780–3191, see Example 1) to a fragment (designated "V2" in FIG. 4) of the cDNA of patatin gene B33. The cDNA contains the signal sequence, mentioned in Implementation Example 3, for uptake into the ER and subsequent guidance into the vacuole; however, the coding region is not interrupted by an intron (Rosahl et al., Mol Gen Genet (1986) 203, 214–220; nt 724–903/1293–1399, sequence derives from pcT58 (counting in accordance with pgT5)). Proteins which possess a signal peptide of this nature are initially taken up into the ER and then transported into the vacuole.

Fragment C contains the polyadenylation signal of gene 3 (Agrobacterium tumefaciens octopine synthase gene) of the T-DNA of the Ti plasmid pTiAch 5 (Gielen et al., EMBO J. (1984) 3, 835–846), that is nucleotides 11749–11939, which was isolated from plasmid pAGV 40 (Herrera-Estrella et al., Nature (1983) 303, 209–213) as a Pvu II/HindIII fragment and, after the addition of SphI linkers, was cloned into the Pvu II cleavage site between the SphI and HindIII cleavage sites of the pBin19-Hyg polylinker.

centrifuged off. The sediment was dissolved in 50 µl of water at 75° C. and precipitated once again with 80% ethanol. The sediment was then dissolved in 30 µl of water at 75° C. and 4 µl aliquots of the solution were analyzed by thin layer chromatography or treated at 56° C. for 15 min with an excess of endoinulinase.

Protocol for the transformation and regeneration of potatoes

The potatoes were transformed and regenerated as described by (Potrykus I., Spangenberg G. (Eds.), 1995, "Gene transfer to plants", Dietze J., Blau A., Willmitzer L., "A Bacteriamediated Transformation of Potato", Springer Lab Manual, pages 24–39).

Working up and isolation of the inulin formed

The potato tubers are washed and then comminuted into gratings using a grater (for example from Nivoba). The gratings are then passed through hydrocyclones using a stream of water and, in conjunction with this, divided into pulp, solids and liquid extract fractions. The solids fraction, which consists in the main of inulin, is purified by washing with water and then dried.

SEQUENCE LISTING

<160> NUMBER OF SEQ ID NOS: 2

<210> SEQ ID NO: 1
<211> LENGTH: 42
<212> TYPE: DNA
<213> ORGANISM: Streptococcus mutans

<400> SEQUENCE: 1
aagcttgatg taccgggccc cccctcgagg tcgacggtat cg          42

<210> SEQ ID NO: 2
<211> LENGTH: 13
<212> TYPE: DNA
<213> ORGANISM: Potato patatin

<400> SEQUENCE: 2
gtcgacggta tcg          13

Plasmid pB33v2ftf is approximately 14 kb in size.

The B33v2ftf construct was introduced into potato plants. Intact plants were regenerated from transformed cells. Analysis of the tubers from a number of plants which were transformed with this gene clearly demonstrated the occurrence of inulin, which is to be attributed to expression of the novel gene.

EXAMPLE 5

Protection of the Formed Inulin.

Protection of the inulin which is formed

Tuber material was homogenized in 100 mM sodium acetate, pH 5.6, in the presence of insoluble polyvinylpyrrolidone (1 ml/100 mg of material), after which the homogenate was incubated at 65° C. for 30 min and then filtered at 65° C. 15 ml of homogenate were incubated at 37° C. for 30 min with 15 µl of RNAse A (1 mg/ml) and 15 µl of DNAse (10 mg/ml), and then at 60° C. for 30 min with 20 µl of proteinaseK (20 mg/ml). Inulin was precipitated from the homogenate by adjusting to 80% ethanol and then

What is claimed is:

1. A modified fructosyltransferase gene derived from Streptococcus mutans and encoding a protein with an inulin sucrase biological activity, wherein the fructosyltransferase gene is modified by having the aminoterminal coding region replaced with a B 33 patatin gene sequence encoding a signal peptide comprising the 60 aminoterminal amino acids of a propeptide encoded by the patatin B 33 gene.

2. The modified fructosyltransferase gene of claim 1, wherein the patatin gene is derived from potato.

3. The modified fructosyltransferase gene of claim 1, wherein the signal peptide allows for uptake of the protein into the endoplasmic reticulum of a eukaryotic cell.

4. The modified fructosyltransferase gene of claim 3, wherein the signal peptide allows for uptake of the protein into a cellular vacuole.

5. The modified fructosyltransferase gene of claim 1 having sequences of another gene located downstream (3') and adjacent of the patatin gene sequence encoding the signal peptide.

6. The modified fructosyltransferase gene of claim 5, wherein the other gene is an Escherichia coli lacZ or carboxypeptidase Y gene.

7. The modified fructosyltransferase gene of claim 1, wherein the region of the fructosyltransferase gene that is replaced is a signal peptide-encoding region.

8. A vector comprising the modified fructosyltransferase gene of claim 1.

9. The vector of claim 8, wherein the modified fructosyltransferase gene is under the control of a promoter active in plants.

10. The vector of claim 9, wherein the promoter is an organ-specific promoter.

11. The vector of claim 9, wherein the promoter is a potato patatin B33 gene promoter.

12. The vector of claim 8, wherein the 3' terminus of the modified fructosyltransferase gene is fused to a transcription terminal signal.

13. The vector of claim 12, wherein the transcription terminal signal is a nos gene polyadenylation site.

14. A process of preparing a recombinantly altered, inulin-producing plant comprising:
  (a) transforming at least one plant cell with the vector of claim 8;
  (b) integrating the modified fructosyltransferase gene in the vector into the genome of transformed cell; and
  (c) regenerating plants which produce inulin.

15. A cell which comprises the modified fructosyltransferase gene of claim 1.

16. The cell of claim 15 which is a bacterial cell.

17. The cell of claim 15 which is a plant cell.

18. A plant comprising the cell of claim 17.

19. A seed of the plant of claim 18.

20. A fruit of the plant of claim 18.

21. A process of obtaining inulin having a molecular weight of more than 1.5 million daltons comprising isolating the inulin from vacuoles of the plant of claim 18.

22. The cell of claim 15 which is selected from the group consisting of a corn, rice, wheat, barley, sugar beet, sugar cane and potato plant cell.

23. A modified fructosyltransferase gene derived from Streptococcus mutans and encoding a protein with an inulin sucrase biological activity, wherein:
  (a) the fructosyltransferase gene is modified by having the aminoterminal coding region replaced with a patatin gene sequence encoding a signal peptide;
  (b) the fructosyl transferase gene has sequences of an Escherichia coli lacZ gene located downstream (3') and adjacent of the patatin gene sequence encoding the signal peptide; and
  (c) the lacZ gene has an aminoterminal region encoding aminoterminal amino acids 21 to 30 of β-galactosidase.

24. A plasmid identified as pB33cftf.
25. A plasmid identified as pB33aftf.
26. A plasmid identified as pB33v1ftf.
27. A plasmid identified as pB33v2ftf.

* * * * *